(12) United States Patent
Hansen et al.

(10) Patent No.: US 7,150,728 B2
(45) Date of Patent: Dec. 19, 2006

(54) COLLECTING BAG HAVING A VENT APERTURE

(75) Inventors: Søren Hansen, Helsingør (DK); Eskil Højland Olsen, Klampenborg (DK)

(73) Assignee: Coloplast A/S, Humlebaek (DK)

( * ) Notice: Subject to any disclaimer, the term of this patent is extended or adjusted under 35 U.S.C. 154(b) by 82 days.

(21) Appl. No.: 10/476,190

(22) PCT Filed: May 8, 2002

(86) PCT No.: PCT/DK02/00299

§ 371 (c)(1),
(2), (4) Date: Nov. 6, 2003

(87) PCT Pub. No.: WO02/089713

PCT Pub. Date: Nov. 14, 2002

(65) Prior Publication Data

US 2004/0143230 A1    Jul. 22, 2004

(30) Foreign Application Priority Data

May 10, 2001 (DK) .......................... PA 2001 00736

(51) Int. Cl.
*A61F 5/441* (2006.01)
*A61F 5/44* (2006.01)
(52) U.S. Cl. ........................ 604/335; 604/333; 604/332
(58) Field of Classification Search ........ 604/327–357; 206/438–439; 383/100–103, 82–85; 600/573–583
See application file for complete search history.

(56) References Cited

U.S. PATENT DOCUMENTS

| | | | | |
|---|---|---|---|---|
| 3,690,320 A | * | 9/1972 | Riley .......................... 604/333 |
| 4,185,630 A |   | 1/1980 | Neumeier et al. .......... 128/283 |
| 4,211,224 A |   | 7/1980 | Kubach et al. ............. 128/283 |
| 4,367,742 A |   | 1/1983 | Ornstein .................... 128/283 |
| 4,372,308 A |   | 2/1983 | Steer et al. ................ 128/283 |
| 4,387,712 A | * | 6/1983 | Briggs et al. ............... 604/333 |
| 4,403,991 A |   | 9/1983 | Hill ............................. 604/337 |
| 4,449,970 A | * | 5/1984 | Bevan et al. ............... 604/333 |
| 4,988,343 A | * | 1/1991 | Ballan ........................ 604/332 |
| 5,865,819 A | * | 2/1999 | Cisko et al. ................ 604/339 |
| 5,968,024 A | * | 10/1999 | Freeman .................... 604/334 |
| 5,976,118 A |   | 11/1999 | Steer .......................... 604/332 |

FOREIGN PATENT DOCUMENTS

EP    0 191 646    8/1986

(Continued)

OTHER PUBLICATIONS

Definitions of "extension" from various online dictionaries.*

*Primary Examiner*—Tatyana Zalukaeva
*Assistant Examiner*—Keshia Gibson
(74) *Attorney, Agent, or Firm*—Jacobson Holman PLLC

(57) ABSTRACT

A collecting bag is provided with a vent aperture to allow for escape of gases which may accumulate in the bag during use. The vent aperture is formed in an extension member that is connected with the bag member. In order to bring the vent aperture from a fully open condition to a fully closed condition, the extension member is folded at least once along a folding line, thereby bringing a first engagement surface into engagement with a second engagement surface. A net element may be positioned between the inlet opening of the bag member and the extension member and a filter device may be positioned within the extension member.

18 Claims, 6 Drawing Sheets

FOREIGN PATENT DOCUMENTS

| | | |
|---|---|---|
| EP | 0 535 801 | 4/1993 |
| EP | 0 709 076 | 5/1996 |
| NO | 166833 | 6/1991 |

* cited by examiner

COLLECTING BAG HAVING A VENT APERTURE

This is a nationalization of PCT/DK02/00299 filed May 8, 2002 and published in English.

1. Field of the Invention

The present invention relates to collecting bags for human body wastes comprising a bag member formed by a first and a second film blank joined along their edges by means of a seam, an inlet opening being provided in one of said film blanks, at least one vent aperture in communication with the interior of the bag member being provided.

2. Background of the Invention

This type of collecting bags are often used as ostomy bags. In order to allow discharge of gases which are accumulated in the bag during use, one or more vent apertures are often provided. Without this precaution the gases would entail a distension of the bag, which might ia. make the bag conspicuous under the user's clothing and thereby cause embarrassment.

EP publication No. 0 535 801 A1 discloses an ostomy bag in which two vent apertures are formed in one of the walls of the bag. The apertures, of which one is provided with a filter, are normally covered by a sealing tape which may be peeled back to expose either the filtered opening or the unfiltered opening in order to allow for the escape of flatus gas.

In the case of ileostomy patients having uncontrolled release of faeces of a relatively fluid consistence, there is generally a great risk of leakage of faecal matter through such a vent aperture.

U.S. Pat. No. 4,185,630 discloses an ostomy pouch which may be brought from its initial non-vented condition to a permanently vented condition by tearing off a protruding portion of the pouch to reveal a gas venting opening. The opening is protected from the contents of the pouch by a discontinuous weld extending transversely of the pouch. The weld comprises an open unwelded portion for allowing passage of gas to the gas venting opening. Although this pouch reduces the likelihood that liquid waste material escapes from the pouch through the vent opening, re-sealing of the vent opening is suggested carried out by applying an adhesive tape or patch at the site of the protruding portion, i.e. a relatively unreliable seal.

SUMMARY OF THE INVENTION

With this background it is an object of the present invention to provide a collecting bag, in which the desired ventilation of the bag may be carried out in a simple manner and which at the same time provides for an improved security with respect to prevention of leakage of the contents of the bag through the vent aperture or apertures, during venting as well as during normal use of the bag.

It is a further object of the invention to provide a collecting bag, in which a filtered ventilation opening may be present and in which the risk of contamination of the filter is reduced.

These and further objects are met by a collecting bag of the initially stated kind, in which said bag member is connected with an extension member extending between a first end proximal to the bag member and a second closed end distal to the bag member, that said at least one vent aperture is provided in said extension member at a distance from said distal end, and that said at least one vent aperture is brought from a fully open condition to a fully closed condition by at least one folding along at least one folding line substantially perpendicular to the longitudinal direction of said extension member to bring a first engagement surface into engagement with a second engagement surface.

By providing the vent aperture on an extension member, the risk of entraining faecal matter contained in the bag member during the venting procedure is substantially reduced, as entrance of this material into the extension member may be prevented manually, eg. by pinching the transition area between the bag member and the extension member and then massaging the material back into the bag member prior to giving access for the gases accumulated in the bag member through the vent aperture. The closed distal end of the extension member improves the security even further. In the fully closed condition, the vent aperture is covered by a part of the folded-over extension member.

In an embodiment, which provides for a particularly secure tightness of the extension member, the at least one vent aperture is provided in the vicinity of the distal end of the extension member. This position entails that a labyrinth seal-like passage is formed between the bag member and the vent aperture or apertures, and the fold itself contributes to the tightness by closing off the passage between the bag member and the vent aperture.

In a preferred embodiment said extension member is formed by a respective extended first and second portion of said film blanks, the edges of said: extended film blank portions being joined along the outer contours of the extension member by means of a continued portion of the seam joining the film blanks in the bag member. This embodiment provides for particularly advantageous production conditions.

In an embodiment, which is a further development of the above-mentioned preferred embodiment, said at least one vent aperture is provided in the first extended film blank portion and the first engagement surface is provided on the second extended film blank portion opposite said at least one vent aperture, and the second engagement surface is provided on the first extended film blank portion at the proximal end of the extension member, the at least one vent aperture being brought to the fully closed condition by two subsequent foldings of the extension member along a first folding line at the proximal edge of the first engagement surface and along a second folding line at the distal edge of the second engagement surface, respectively. In this manner, the extension member may be designed with a certain, substantial length, which increases the security against leakage of faecal material through the vent aperture and nevertheless be brought to a folded-over position close to the bag member, corresponding to the fully closed condition, thereby preventing the extension member from dangling and chafing against the user's skin.

In an alternative further development of the preferred embodiment, said at least one vent aperture is provided in the first extended film blank portion and the first engagement surface is provided on the first extended film blank portion, the distal edge of the first engagement surface being positioned at a distance from the at least one vent aperture, and the second engagement surface surrounds the at least one vent aperture, a third engagement surface being provided on the first extended film blank portion, the distal edge of the third engagement surface being positioned at a distance from the proximal edge of the first engagement surface corresponding substantially to the distance between the proximal and distal edges of the first engagement surface, the at least one vent aperture being brought to the fully closed condition by three subsequent foldings of the extension member along a first folding line at the distal edge of the first engagement surface for bringing the first and second engagement surfaces into mutual engagement, along a second folding line at the proximal edge of the first engagement surface, and along a third folding line at the distal edge of the third engagement surface, respectively.

The engagement surfaces may include mutually interlocking and releasably engageable elements, such as locking elements comprising hooks and eyes, Velcro elements, etc., or releasable adhesive layers, which may advantageously include a supporting plate underlying said layer of adhesive.

In case at least the first engagement surface of the above-mentioned alternative further development of the preferred embodiment includes a layer of releasable adhesive, the second extended film blank portion may advantageously be brought into engagement with said first engagement surface in connection with the initial folding along the first folding line. This provides for a particularly tight seal of the extension member in the fully closed condition.

In order to make the folding procedure logical and clear to the user, each folding line may be indicated by a score line embossed into the extension member.

In order to facilitate the pinching-off of the extension member, this member may have a relatively narrow extent in the transverse direction.

Furthermore, the extension member may positioned in the upper region of the bag, which increases the security against dirtying of the extension member during normal usage of the collecting bag.

In order to reduce the risk of contaminating the vent aperture even further, a net element may be positioned between the inlet opening of the bag member and the extension member.

The bag may furthermore comprises a filter device, which makes it possible to deodorize any escaping gas to avoid embarrassing odour.

In an advantageous embodiment, the filter device is positioned within the extension member which provides for a particularly protected position of the filter, whereby contamination of the filter may be substantially reduced.

The filter device may be positioned in a space provided in the extension member and having an outlet opening separated from said at least one vent aperture, said space being in communication with the bag member such that in the fully closed condition, gas may ooze or leak through said outlet opening. By this design a protection against contamination is achieved while simultaneously giving the possibility of combining a controlled release of gas through the vent aperture and a continuous ooze through the filtered opening.

Further features and advantages may readily be appreciated from the following detailed description.

BRIEF DESCRIPTION OF THE DRAWINGS

In the following the invention will be described in further detail with reference to preferred embodiments and the several views of the schematic drawings, in which.

DETAILED DESCRIPTION OF PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
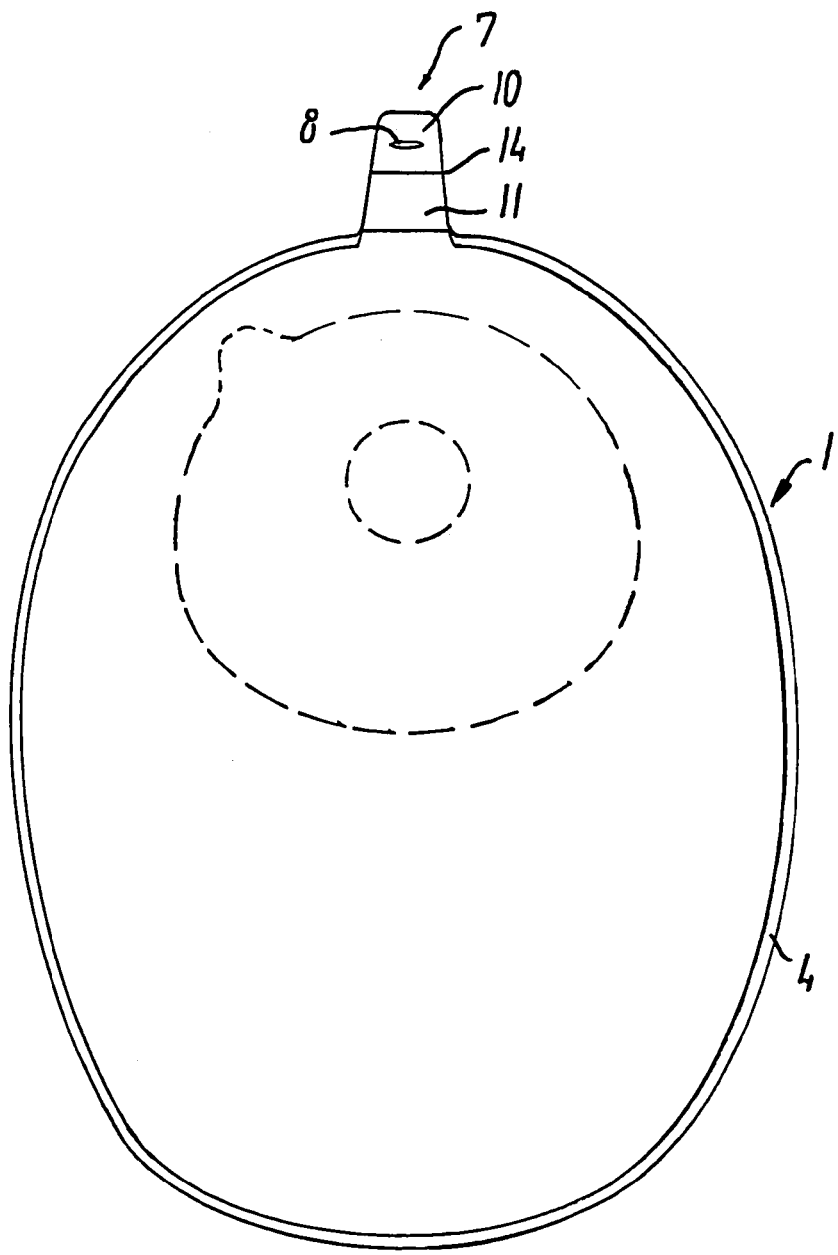
FIG. 1 shows a plan view of a first embodiment of a collecting bag according to the invention, seen from the side intended to face away from the user and in the fully open position.
Figure 2:
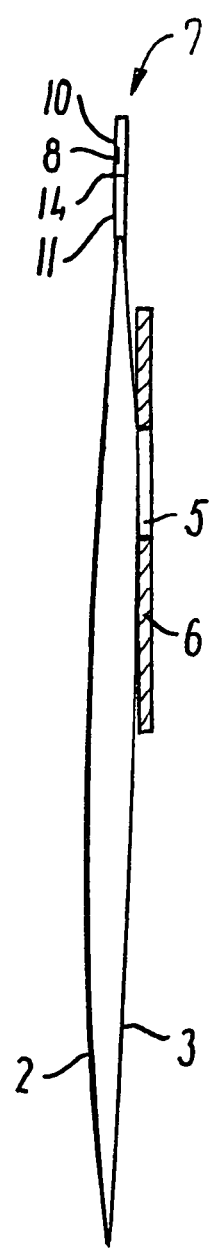
FIG. 2 shows a longitudinal section of the collecting bag of FIG. 1.

The collecting bag of the first embodiment, shown in FIGS. 1 and 2, comprises a bag member 1 which is formed by a first film blank 2 forming the front wall of the bag and which in use is positioned to face away from the user, and a second film blank 3 forming the back wall of the bag. The two film blanks 2, 3 are joined along their outer contours by means of a seam 4 which is provided by eg. welding or heat-sealing the film blanks. In the second film blank 3, which in use faces the user, an inlet opening 5 is provided for receiving an end portion of the intestines of the user. The bag is fastened to the user by means of connecting elements 6.

In the embodiment shown, the bag is not provided with outlet means for emptying the bag of its contents. Such outlet means may in a manner known per se be provided in the lower portion of the bag member. In this respect it is noted that terms such as "upper" and "lower" etc. only refer to the position, the bag assumes when the user is eg. standing or sitting upright.

In the upper region of the bag, arrangement has been made to allow for escape of gases which may accumulate in the bag during use. This arrangement comprises an extension member generally designated 7, in which one or more vent apertures have been formed In principle such an extension member 7 may comprise eg. a tube member having a closed end and which at the opposite end is fastened to the bag member in any appropriate manner, a vent aperture 8 being provided at any point between the two ends of the extension member and two engagement surfaces 10, 11 being provided to close off the vent aperture in connection with a single folding operation along a folding line 14. The engagement surfaces 10, 11 may eg. include a releasable adhesive on at least one of the engagement surfaces, or may include mutually interlocking and releasably engageable elements such as hook and eye closures, eg. of the Velcro type.

In the following a detailed description of a second embodiment will be given with reference to FIGS. 3 and 4.

The collecting bag of this embodiment comprises a bag member 101 which is formed by a first film blank 102 forming the front wall of the bag and which in use is positioned to face away from the user, and a second film blank 103 forming the back wall of the bag. The two film blanks 102, 103 are joined along their outer contours by means of a seam 104 which is provided by eg. welding or heat-sealing the film blanks. In the second film blank 103, which in use faces the user, an inlet opening 105 is provided for receiving an end portion of the intestines of the user. The bag is fastened to the user by means of connecting elements 106.

Figures 3, 4:
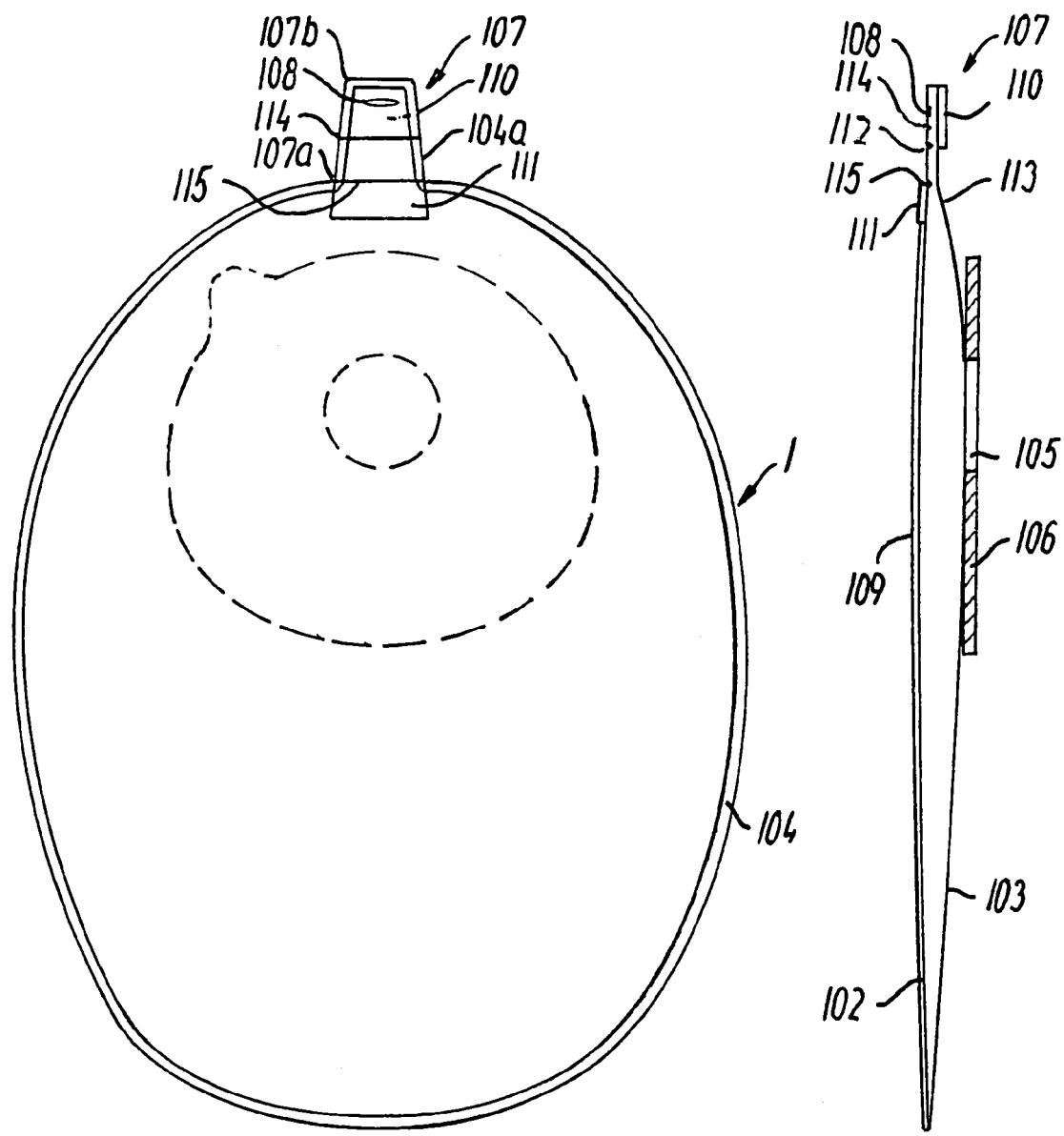
FIG. 3 shows a plan view of a second embodiment of a collecting bag according to the invention, seen from the side intended to face away from the user and in the fully open position.
FIG. 4 shows a longitudinal section of the collecting bag of FIG. 3.

In the second embodiment shown in FIGS. 3 and 4, the extension member 107 is formed by extended film blank portions 112 and 113 of the first and second film blanks 102 and 103, respectively, of the bag member 101. The edges of the extended film blank portions 112 and 113 of the extension member 107 are joined by means of a portion 104a of the seam 104 such that the film blanks of the bag member 101 and the extension member 107 are joined in eg. a continuous welding operation.

The extension member 107 is in the embodiment of FIGS. 3 and 4 of an elongate configuration and extends between a first end 107a proximal to the bag member 101 and a second end 107b remote or distal to the bag member 101. It is noted that the second end 107b is closed by means of the continued seam portion 104a. In the vicinity of ie. at a small distance from the closed second end 107b a vent aperture 108 is formed in the first extended film blank portion 112. The vent aperture could in principle have another position, as long as it is covered by the engagement surfaces following the mutual engagement between the engagement surfaces. However, it is preferred that the vent aperture be positioned on the distal side of the folding line or lines. Opposite the vent aperture 108 there is a first engagement surface 110 on the second extended film blank portion 113. In the fully open condition, gases accumulated in the bag member 101 are free to escape via the passage formed between the extended film blank portions 112 and 113 and out through the vent aperture 108. In order to bring the collecting bag into its normal use condition, ie. to close the vent aperture 108, the extension member 107 is folded over twice along a first and a second folding line 114 and 115, each of which extends substantially perpendicular to the longitudinal direction of the extension member 107 to bring the first engagement surface 110 into contact with a second engagement surface 111 positioned in the transition area between the bag member 101 and the extension member 107, advantageously within the outer contours of the bag member 101. By the mutual engagement between the engagement surface, the vent aperture is closed and virtually no gas may escape.

The engagement surfaces 110 and 111 may include mutually interlocking and releasably engageable elements such as hook and eye closures, eg. of the Velcro type. Alternatively, the engagement surfaces may include layers of a releasable adhesive. In case releasable adhesive layers are used, a supporting plate underlying at least one of said layers may be provided in order to facilitate the folding operation and/or to improve the tightness of the vent aperture by reducing the risk of penetration of faecal matter and gas into the passage and out through the vent aperture. The folding lines 114 and 115 may furthermore be indicated visually and palpably by score lines embossed into the extension member, which makes the folding procedure logical and clear to the user. The dimensions of the engagement surfaces may be chosen arbitrarily, as long as they fulfill the demands made to a secure engagement, but are preferably designed such that each engagement surface extends throughout the width of the extension member, ie. in the transverse direction thereof, and such that the first engagement surface 110 extends in the longitudinal direction from the distal end 107b to the first folding line 111 and the distal edge of the second engagement surface should be positioned at a distance from the first folding line 111 corresponding to the longitudinal dimension of the first engagement surface 110.

In case the engagement surfaces include a hook and eye closure, the hook part may be utilized in the first engagement surface 110 and the eye part in the second engagement surface 111, or vice versa. In case the collecting bag is provided with a comfort layer 109 which overlies the second film blank 102 of the bag member 101, the second engagement surface 111 may be constituted by a portion of this comfort layer 109, provided the latter is of an appropriate material to cooperate with the first engagement surface 110.

Figure 5:
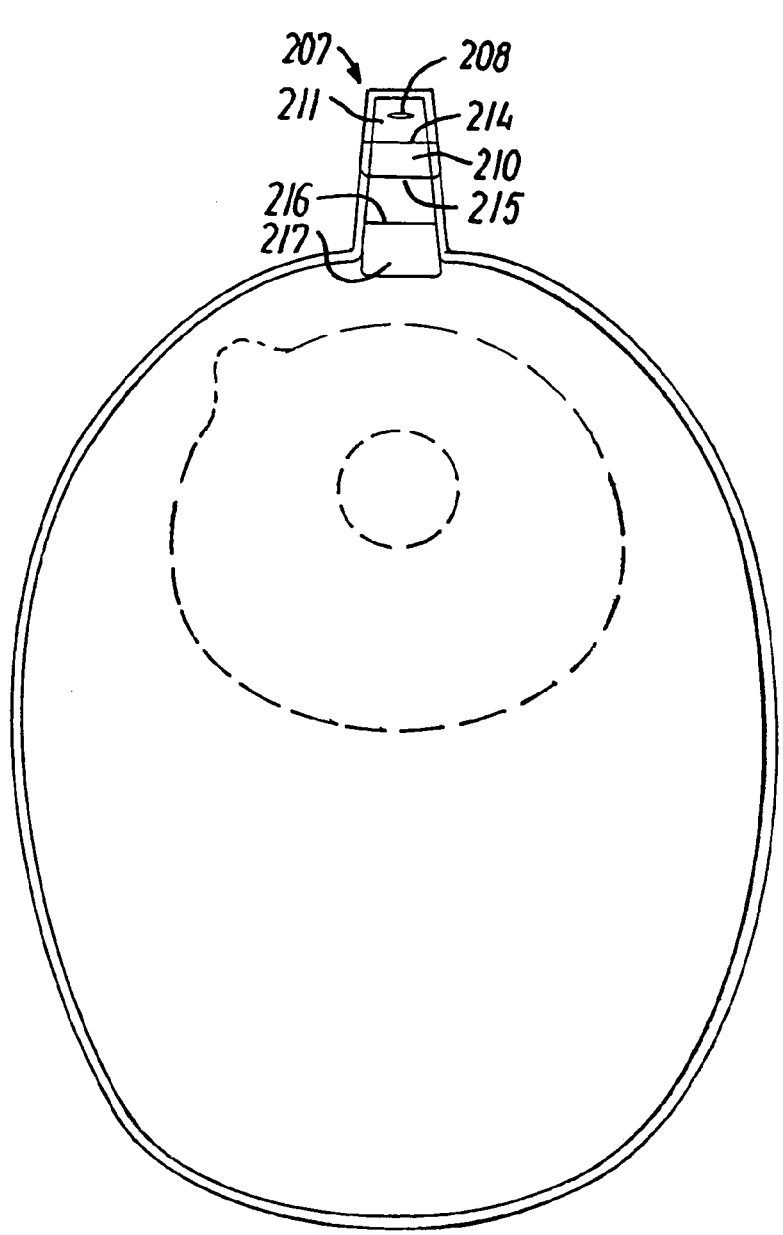
FIG. 5 shows a plan view of a third embodiment of a collecting bag according to the invention, seen from the side intended to face away from the user and in the fully open position.
Figure 6:
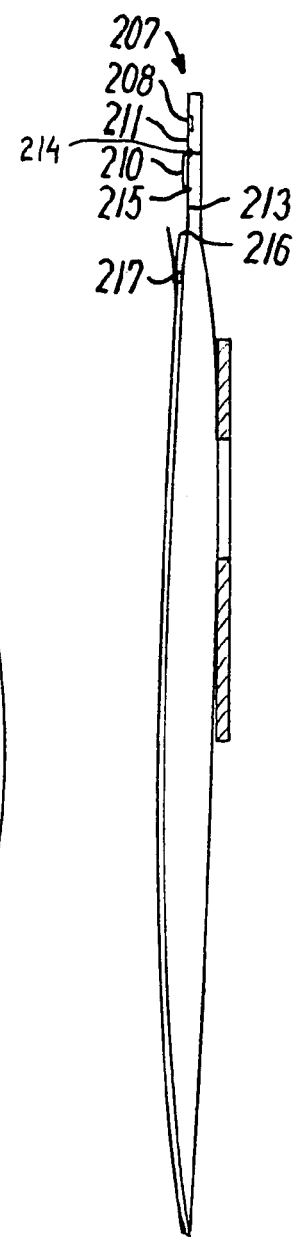
FIG. 6 shows a longitudinal section of the collecting bag of FIG. 5.
Figure 7:
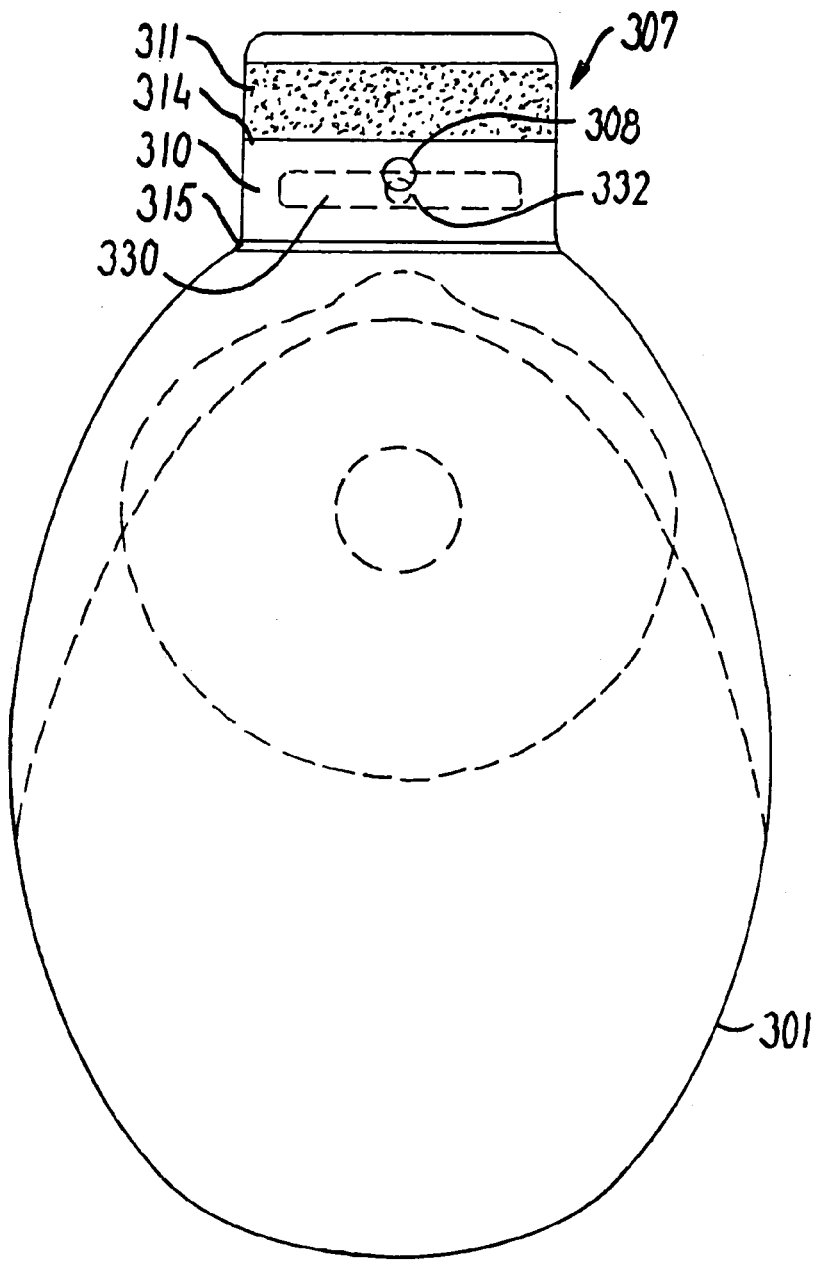
FIG. 7 shows a plan view of a fourth embodiment of a collecting bag according to the invention, seen from the side intended to face away from the user and in the fully closed position.
Figure 10:
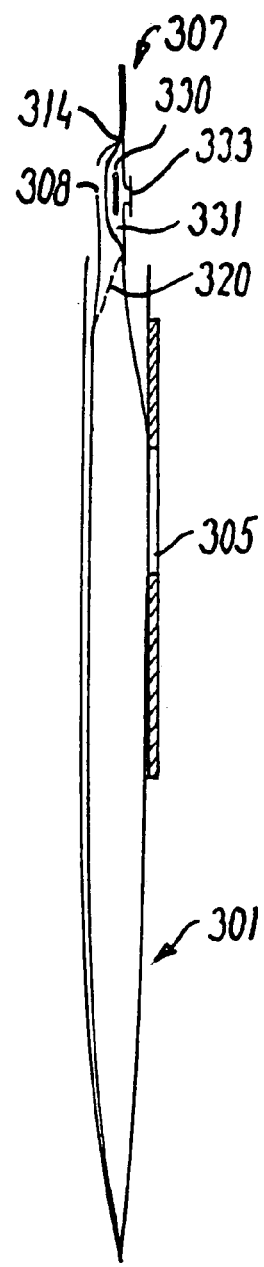
FIG. 10 shows a longitudinal section of the fourth embodiment of collecting bag in the position shown in FIG. 7.
Figure 8:
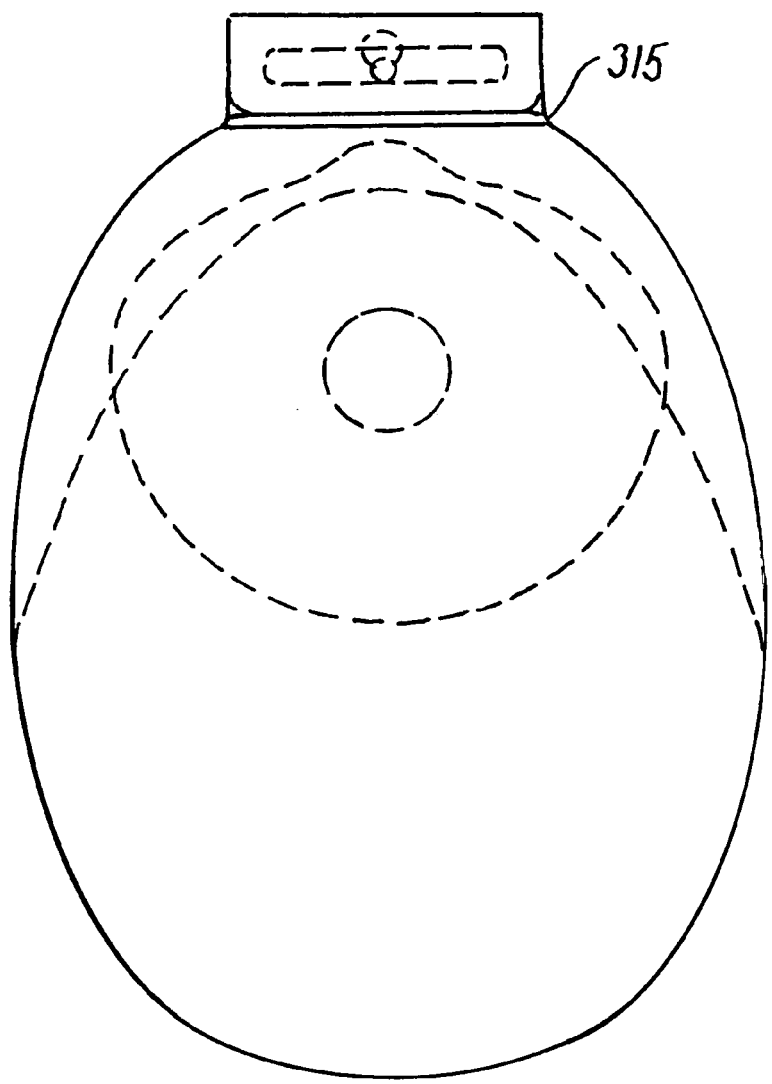
FIG. 8 shows a plan view of the collecting bag of FIG. 7 in which the first and second engagement surfaces have been brought into mutual engagement.
Figure 11:
FIG. 11 shows a longitudinal section of the fourth embodiment of collecting bag in the position shown in FIG. 8.
Figure 9:
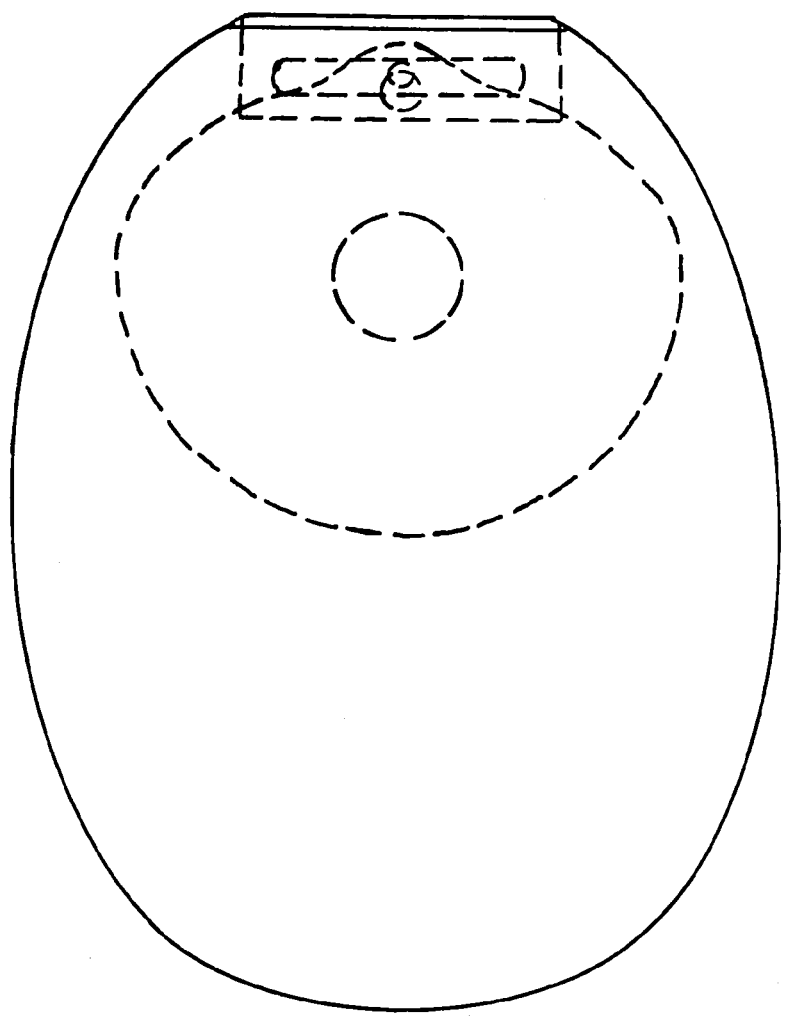
FIG. 9 shows a plan view of the collecting bag of FIG. 7 in which the extension member has been folded over twice to assume a position corresponding to the condition of the bag during normal use.
Figure 12:
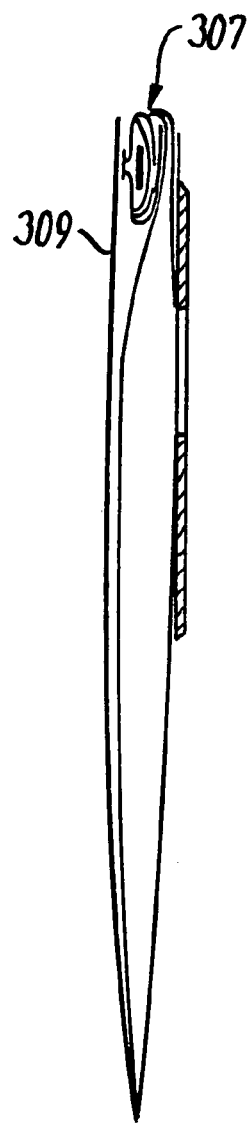
FIG. 12 shows a longitudinal section of the fourth embodiment of collecting bag in the position shown in FIG. 9.

The third embodiment of the collecting bag according to the invention, shown in FIGS. 5 and 6, has several structural similarities to the first and in particular the second embodiment. Hence, elements having the same or analogous function as in the second embodiment carry the same reference numerals to which 100 has been added and only differences from the second embodiment will be described in detail.

In the third embodiment the vent aperture 208 is surrounded by the second engagement surface 211, and the first engagement surface 210 is positioned immediately proximal to the second engagement surface, separated by the first folding line 214. By initial folding of the extension member 207 along the first folding line 214, the vent aperture 208 is covered. In case at least the first engagement surface 210 includes an adhesive layer, the second extended film blank portion 213 is brought into contact with and adheres to the first engagement surface 210 through the vent aperture 208. This provides for a particularly fluid tight sealing of the vent aperture. By subsequent folding of the extension member 207 along the second folding line 215 at the proximal edge for the first engagement surface 210, and subsequently along a third folding line 216, the folded-over portion of the extension member 207 may be brought into contact with a layer of adhesive included in a third engagement surface 217 at the proximal end of the extension member 207, advantageously within the outer contours of the bag member 201. Alternatively, the first and second engagement surfaces 210, 211 may include a hook and eye closure such as Velcro.

It is noted that in all of the above embodiments the extension member 7, 107, 207 has a relatively narrow shape, ie. a small extent in the transverse direction, ia. in order to minimize the amount of liquid faecal matter which may find its way into the passage leading to the vent aperture. When the collecting bag is to be vented, the user may pinch off the transition area between the bag member and the extension member prior to releasing the engagement between the first and second engagement surfaces and then stroke or massage the extension member in the direction of the bag member in order to force the faecal matter back into the bag member.

In the following a description will be made of a fourth embodiment of the invention, which is shown in FIGS. 7 to 12. Elements having the same or analogous function as corresponding elements of the second embodiment carry the same reference numerals to which 200 has been added and only differences from the second embodiment will be described in detail.

In this embodiment, faecal matter is received through the inlet opening 305 to a portion of the bag member 301 which is separated from the portion of the bag member which communicates with the extension member 307 by means of a net element 320 of a type known per se, ie. of a gas-permeable but liquid-impermeable material. The net element 320 prevents or at least reduces the amount of liquid faecal material which may enter into the extension member 307 and thus to the vent aperture 308. The net element 320 may have various shapes, ranging from a small element extending over the inner area of the bag member 301 in the vicinity of the extension member 307, to an element constituting a partition wall which is positioned between the first and second film blanks 302 and 303 of the bag member 301.

Furthermore, the collecting bag ot this element is provided with a filter device 330 positioned within the extension member 307. The filter device 330 is positioned in a space 331 provided in the extension member 307 and has an outlet opening 332 separated from the vent aperture 308. The space 331 is in communication with the bag member 301 such that in the fully closed condition, shown in FIGS. 9 and 12, gas may ooze or leak through the outlet opening 332 which is covered by a liquid-impermeable membrane 333. It is of course conceivable to position a filter in e.g. one of the film blanks as well, and it is furthermore possible to use the filter device without the net element. The procedure of closing the vent aperture 308 may be seen sequentially in FIGS. 7 to 9 and 10 to 12, respectively. As shown, the second engagement surface 311 is folded along the first folding line 314 to be brought against the first engagement surface 310, followed by a subsequent fold along second folding line 315. Tn the resulting position shown in FIGS. 9 and 12, the extension member 307 is concealed under the comfort layer 309 in order to provide optimum comfort to the user.

The invention should not be regarded as being limited to the embodiments described in the above but various modifications and combinations of the shown embodiments may be carried out without departing from the scope of the following claims.

For example, although the invention has been described only with reference to ostomy bags not having an outlet opening for emptying and re-use of the bag, it is of course possible to apply the invention to that form of collecting bag as well. Furthermore, more than one vent aperture may be provided, and the extension member may have other shapes and positions than the ones shown in the above.

The invention claimed is:

1. A collecting bag for human body wastes comprising a bag member formed by a first and a second film blank joined along their edges by a seam, an inlet opening being provided in one of said film blanks, at least one vent aperture in communication with the interior of the bag member being provided, said bag member being connected with an extension member formed by first and second extended portions of said first and second film blanks, respectively, said extension member being positioned in an upper region of the bag and extending between a first end of said extension member proximal to and joined with the bag member and a second closed end of said extension member distal to and spaced from the bag member, said at least one vent aperture being provided in the first extended film blank portion of said extension member at a distance from said distal end, said at least one vent aperture being brought from a fully open condition to a fully closed condition by at least one folding along at least one folding line substantially perpendicular to the longitudinal direction of said extension member to bring a first engagement surface into engagement with a second engagement surface, said at least one vent aperture being covered by a part of the folded-over extension member in said fully closed position.

2. The collecting bag as claimed in claim 1, wherein said at least one vent aperture is provided in the vicinity of the distal end of the extension member.

3. The collecting bag as claimed in claim 2, wherein the edges of said extended film blank portions are joined along the outer contours of the extension member by a continued portion of the seam joining the film blanks in the bag member.

4. The collecting bag as claimed in claim 3, wherein said at least one vent aperture is provided in the first extended film blank portion and the first engagement surface is provided on the second extended film blank portion opposite said at least one vent aperture, and that the second engagement surface is provided on the first extended film blank portion at the proximal end of the extension member, the at least one vent aperture being brought to the fully closed condition by two subsequent foldings of the extension member along a first folding line at the proximal edge of the first engagement surface and along a second folding line at the distal edge of the second engagement surface, respectively.

5. The collecting bag as claimed in claim 3, wherein said at least one vent aperture is provided in the first extended film blank portion and the first engagement surface is provided on the first extended film blank portion, the distal edge of the first engagement surface being positioned at a distance from the at least one vent aperture, and the second engagement surface surrounds the at least one vent aperture, a third engagement surface being provided on the first extended film blank portion, the distal edge of the third engagement surface being positioned at a distance from the proximal edge of the first engagement surface corresponding substantially to the distance between the proximal and distal edges of the first engagement surface, the at least one vent aperture being brought to the fully closed condition by three subsequent foldings of the extension member along a first folding line at the distal edge of the first engagement surface for bringing the first and second engagement surfaces into mutual engagement, along a second folding line at the proximal edge of the first engagement surface, and along a third folding line at the distal edge of the third engagement surface, respectively.

6. The collecting bag as claimed in claim 1, wherein said engagement surfaces include mutually interlocking and releasably engageable elements.

7. The collecting bag as claimed in claim 1, wherein said engagement surfaces include releasable adhesive layers.

8. The collecting bag as claimed in claim 7, wherein at least one of said engagement surfaces includes a supporting plate underlying said layer of adhesive.

9. The collecting bag as claimed in claim 5, wherein said second extended film blank portion is brought into engagement with said first engagement surface in connection with the initial folding along the first folding line.

10. The collecting bag as claimed in claim 1, wherein said folding line is indicated by a score line embossed into the extension member.

11. The collecting bag as claimed in claim 1, wherein the extension member has a relatively narrow extent in the transverse direction.

12. The collecting bag as claimed in claim 1, wherein a net element is positioned between the inlet opening of the bag member and the extension member.

13. The collecting bag as claimed in claim 1, wherein the bag includes a filter device.

14. The collecting bag as claimed in claim 13, wherein said filter device is positioned within the extension member.

15. The collecting bag as claimed in claim 14, wherein the filter device is positioned in a space provided in the extension member and having an outlet opening separated from said at least one vent aperture, said space being in communication with the bag member such that in the fully closed condition, gas may ooze or leak through said outlet opening.

16. A collecting bag for human body wastes comprising a bag member formed by a first and a second film blank joined along their edges with an inlet opening being provided in one of said film blanks, said bag member having an extended film blank portion forming an elongated extension member positioned in the upper region of the bag with a first end proximal to the bag member, a second closed end distal to the bag member, and a folding line between said first and second ends that extends transversely across said extension member substantially perpendicular to a longitudinal length of said extension member, at least one vent aperture in said extension member in communication with the interior of the bag member and spaced from said distal end, said at least one vent aperture being brought from a fully open condition to a fully closed condition by at least one folding of said extension member upon itself along said folding line to bring a first engagement surface on said extension member into secure and releasable engagement with a second engagement surface proximal to said first engagement surface, said second engagement surface also being proximal to said first engagement surface prior to said folding.

17. A collecting bag for human body wastes comprising a bag member formed by a first and a second film blank joined along their edges by a seam with an inlet opening being provided in one of said film blanks, said bag member being joined with an extension member by a welded or heat-sealed seam, said extension member being positioned in an upper region of the bag and having a first end proximal to the bag member, a second closed end distal to the bag member, and first and second engagement surfaces thereon that are mutually cooperative for secure and releasable engagement with one another, at least one vent aperture in said extension member in communication with the interior of the bag member and spaced from said distal end, said at least one vent aperture being brought from a fully open condition to a fully closed condition by at least one folding along at least one folding line substantially perpendicular to a longitudinal direction of said extension member to bring said first engagement surface into engagement with said second engagement surface to cover said vent.

18. A collecting bag for human body wastes comprising a bag member formed by a first and a second film blank joined along their edges by a seam, an inlet opening being provided in one of said film blanks, said bag member having an extension member positioned in the upper region of the bag with a first end proximal to the bag member and a second closed end distal to the bag member at least one vent aperture in communication with an interior of said bag member being provided in said extension member at a distance from said distal end, and said at least one vent aperture being brought from a fully open condition to a fully closed condition by a first folding of said extension member along a first folding line substantially perpendicular to a longitudinal direction of said extension member to bring a first engagement surface on said extension member into engagement with a second engagement surface proximal to said first engagement surface and a second folding along a second folding line substantially parallel with said first folding line.

* * * * *